US005349070A

United States Patent [19]

Han

[11] Patent Number: 5,349,070

[45] Date of Patent: Sep. 20, 1994

[54] SALICYLIC ACID-MALTOL CONJUGATES

[76] Inventor: Byung H. Han, 31-34, Jongam-dong, Seungbuck-ku, Seoul 136-090, Rep. of Korea

[21] Appl. No.: 971,832

[22] PCT Filed: Jun. 21, 1991

[86] PCT No.: PCT/KR91/00015

§ 371 Date: Feb. 19, 1993

§ 102(e) Date: Feb. 19, 1993

[87] PCT Pub. No.: WO93/00339

PCT Pub. Date: Jan. 7, 1993

[51] Int. Cl.$^5$ .......... C07D 309/40

[52] U.S. Cl. .......... 549/417

[58] Field of Search .......... 549/417

[56] References Cited

U.S. PATENT DOCUMENTS 5,075,461 12/1991 Wild .......... 549/417

OTHER PUBLICATIONS

Pedersen, et al. *The New England Journal of Medicine,* 311(19):1207-1211 (1984).

H. J. M. Barnett *Stroke,* 21(suppl IV):IV-40-IV-43 (1990).

B. Han et al. *Korean Biochem. J.* 18(4):337-340 (1985).

A. J. Cameron Mayo Clinic Proceedings, vol. 50: 565-570 (1975).

Manekar et al. *Indian J. Med. Res.,* 71:926-932 (1980).

K. D. Rainsford, *Br. J. exp. Path.,* 58:215 (1977).

H. W. Davenport Gastroenterology, 46(3):245-253 (1964).

*Primary Examiner*—Nicky Chan

*Attorney, Agent, or Firm*—Birch, Stewart, Kolasch & Birch

[57] ABSTRACT

The present invention relates to a novel salicylic acid-maltol conjugates of the formula I.

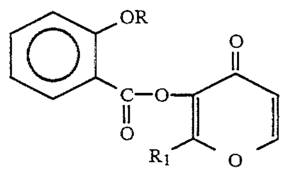

(I)

wherein R represents H, alkyl groups containing $C_{1-5}$ carbon atoms or alkanoyl groups containing $C_{1-5}$ carbon atoms. $R_1$ represents H or alkyl groups containing $C_{1-5}$ carbon atoms.

A novel maltol esters of salicylic acid derivatives exhibit antioxidant and antithrombotic activities to a greater extent than salicylic acid derivatives.

1 Claim, 3 Drawing Sheets

FIG. I

SALICYLIC ACID-MALTOL CONJUGATES

DETAILED DESCRIPTION OF THE INVENTION

The present invention relates to a novel salicylic acid-maltol conjugates of the formula I and methods for preparing I.

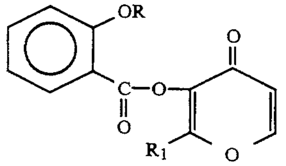

(I)

wherein R represents H, alkyl groups containing $C_{1-5}$ carbon atoms or alkanoyl groups containing $C_{1-5}$ carbon atoms. $R_1$ represents H or alkyl groups containing $C_{1-5}$ carbon atoms.

Acetylsalicylic acid (aspirin) shows antipyretic, antianalgesic, antioxidant and antithromobotic activities. However, it induces gastric ulceration.

Maltol derivatives II are components of *Panax ginseng* and their structures are as follows:

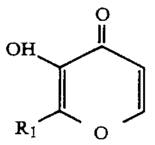

(II)

wherein $R_1$ is as previously defined. Maltol derivatives have been shown to exhibit antioxidant activities. Salicylic acid has been used as a keratolytic agent and a food preservative.

The present invention follows the observations that the novel maltol esters of salicylic acid derivatives show no salicylate-induced gastric ulceration activity, whereas exhibit antioxidant and antithrombotic activities to a greater extent than salicylic acid derivatives.

Therefore, the purpose of the presented invention is to provide the novel of the formula I which exhibit aforementioned pharmacological activities and little side effects.

The present invention also provides the synthetic methods of compounds I. Compounds of the formula I are prepared with esterficiation of maltol derivatives II and salicylic acid derivatives III as follows:

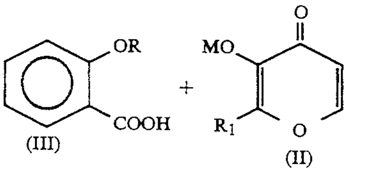

(III) (II)

-continued

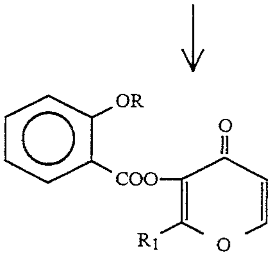

(I)

wherein R and $R_1$ are as described above and M is $-H$ or an alkali metal.

The esterification of II with III can be done in the presence of either alkyl halides such as chloroform, methylenechloride and ethylenechloride, or amides such as formamide and acetamide, or ethers such as tetrahydrofuran and dioxane, or other organic solvents.

It is desirable to activate the carboxyl group of III. The activation can be achieved by treating III with halogenation agents to make acid halides or by other well-known methods used in organic synthesis.

The reaction of II with III which contains a carboxyl group can be carried out in the presence of diamines such as N,N-dicyclohexylcarbodiimide or other esterification agents used in organic synthesis.

In case free acids are produced in the activation of the carboxyl group, the esterification should be conducted in the presence of tertiary amines or alkalis to remove the free acids.

The reaction is proceeded at the temperature ranging from 0° C. to the b.p. of the solvent employed. The reaction usually goes to completion in 30 min to 48 hrs.

The present invention will now be described with the following examples and tests.

EXAMPLE 1

Acetylsalicylic acid (18.0 g, 0.10 mole), maltol (12.6 g, 0.10 mole), N,N-dicyclohexylcarbodiimide (22.7 g, 0.11 mole) were dissolved in 100 ml of methylenechloride and the solution was stirred for 6 hrs at room temperature.

Figure 1:
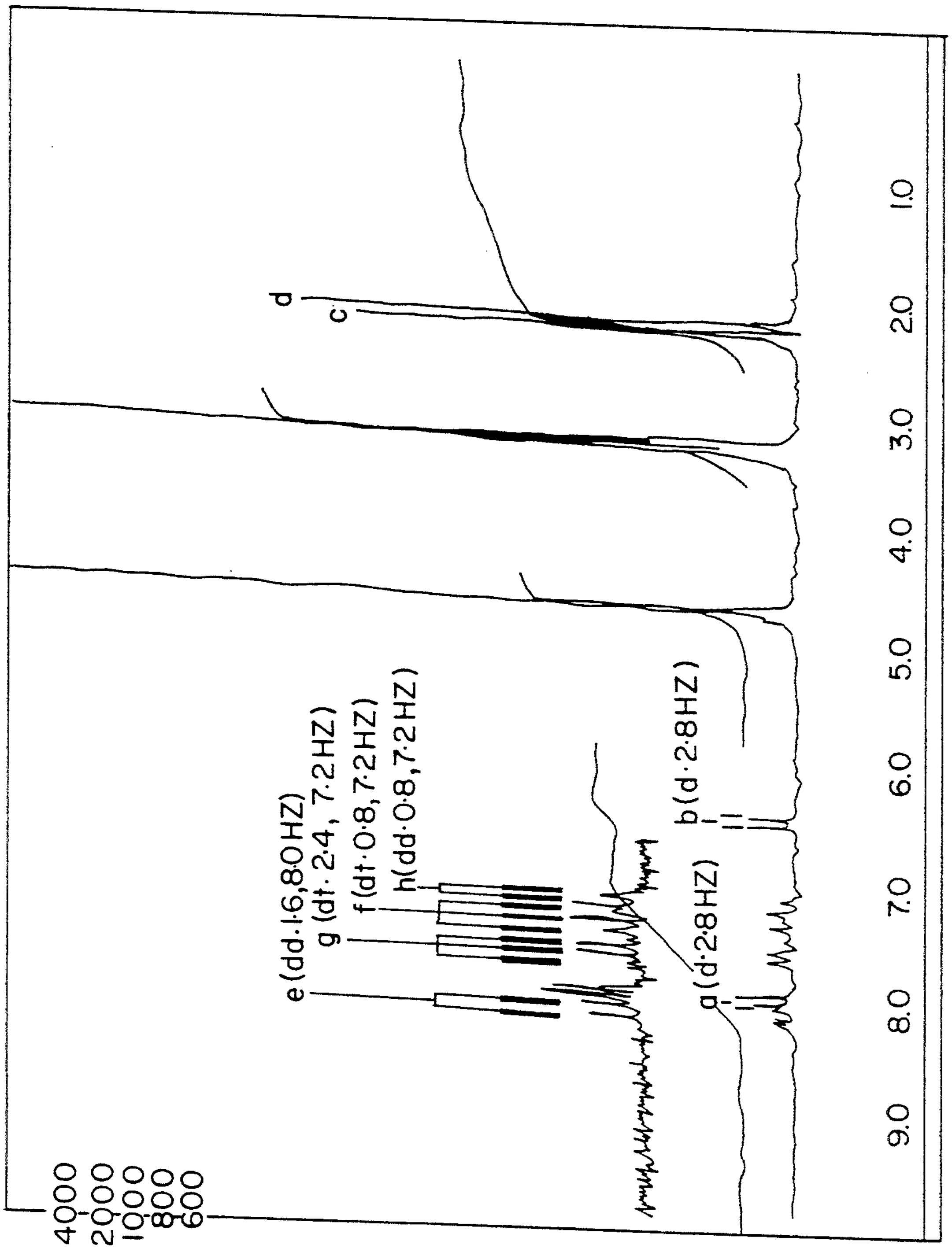
FIG. 1 illustrates the NMR spectrum of maltol-acetylsalicylate ester.

After removing N,N-dicyclohexylurea by filtration, the filtrate was washed sequantially with water, 5% acetic acid and water. The solution was then dried with $Na_2SO_4$. Following filtration and concentration, the needle crystal of maltol-acetylsalicylate ester (compound A) was obtained in n-hexane/ethanol (1:3). NMR spectrum is shown in FIG. 1.

mp: approximately 105° C.

MS [m/z]:288($M^+$), 246($C_{13}H_{10}O_5$), 121($C_7H_5O_2$).

$^1H$ NMR ($CDCl_3$) [δ ppm]:8.21(1H, dd, J=1.9, 7.7), 8.07(1H, d, J=5.7), 7/74(1H, dt, J=1.9, 7.7), 7.43(1H, dt, J=1.3, 7.7), 7.24(1H, dd, J=1.3, 7.7) 6.48(1H, d, J=5.6), 2.32(3H, s), 2.25(3H, s).

EXAMPLE 2

Figure 2:
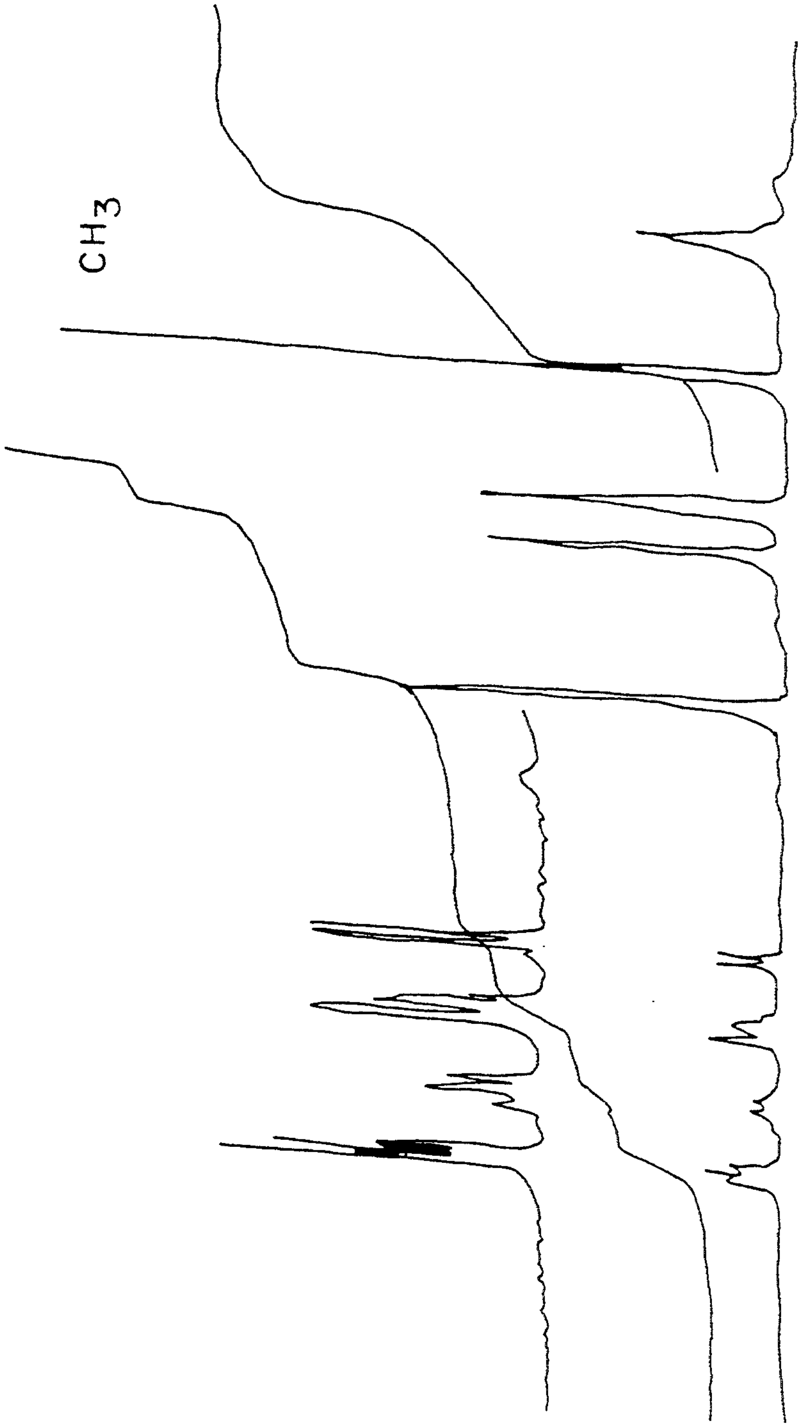
FIG. 2 illustrates the NMR spectrum of maltol-salicylate ester.

Maltol-salicylate ester was obtained following the method of Example 1. NMR spectrum is shown in FIG. 2.

mp: approximately 99° C.

EXAMPLE 3

Enzymetic Method of Maltol-Salicylate Ester Preparation

An aceton powder (1.8 g) of rat livers was suspended in 50 ml of 0.1M phosphate buffer (pH 7.4) and stirred for 12 hrs at 4° C. The resulting suspension was centrifuged at 8,000 rpm for 5 min. To 10 ml of supernatant thus obtained was added 30 ml of 10% Tween-30 solution containing maltol-acetylsalicylate ester. The mixture was incubated at 37° C. for 1 hr, and extracted twice with 30 ml of $CHCl_3$. The extracts were then added and concentrated to dryness. The dried residue was dissolved in 5 ml of methanol and allowed to stand at 4° C. Following filtration, 200 mg of maltol-salicylate ester was obtained as the needle crystal. NMR spectrum was equivalent to that obtained in Example 2.

TEST 1

Determination of Antioxidant Activity

Animal: male ICR mouse weighing 20–25 g
Sample: Compound A.
References:
1. Maltol (10% DMF saline)
2. Aspirin (10% DMF saline).

TBA reagents: Thiobarbituric acid (0.3%) and SDS (0.4%) were dissolved in 7.5% acetate buffer (pH 4.0)

Experimental Procedures

Antioxidant activities were determined following the method of Okawa et al. (*Biochemistry* (Japan) 1977), 49(8), 829). Mouse livers were homogenized with ten volumes of saline. To 10 ml of homogenate was added 10 ml of the sample solution, and the mixture was incubated at 37° C. for 3 hrs. Then 3.6 ml of TBA reagents were added to the mixture and the resulting mixture was heated at 98° C. for 1 hr. After the temperature was reduced to 24° C., the reaction mixture was extracted with 2 ml of butanol and the butanol phase was separated by centrifugation. The absorbance at 532 nm of the butanol phase was measured. The results are shown in Table I. Compound A exhibited antioxidant activity at concentrations higher than 2.5×10M.

TABLE I

Antioxidant Activities of Maltol, Aspirin and Maltol-Acetylsalicylate ester (Compound A). % Inhibition of Malondialdehyde (MDA) Generation in Mouse Liver Homogenate (in vitro)

| Final Concentration | % Inhibition | | |
|---|---|---|---|
| (M) | Maltol | Aspirin | Compound A |
| $1.3 \times 10^{-5}$ | 5.2 ± 2.6 | — | 4.3 ± 2.1 |
| $6.3 \times 10^{-5}$ | 13.4 ± 6.7 | 4.6 ± 2.3 | 2.3 ± 1.1 |
| $2.5 \times 10^{-4}$ | 94.8 ± 2.6 | 0.8 ± 0.4 | 58.9 ± 7.0 |
| $2.5 \times 10^{-3}$ | 99.4 ± 0.3 | 8.4 ± 4.2 | 91.9 ± 4.1 |

TEST 2

Determination of Antipyretic Activity

Animal: Male ICR mouse weighing 17–21 g (5 mice as a group).
Sample: Compound A (160 mg/kg, 500 mg/kg in 1% CMC).
Reference: Aspirin (100 mg/kg in 1% CMC).
Pyrogen: Typhoid vaccine (0.1 ml/mouse, i.p.).

Experimental Procedures

Figure 3:
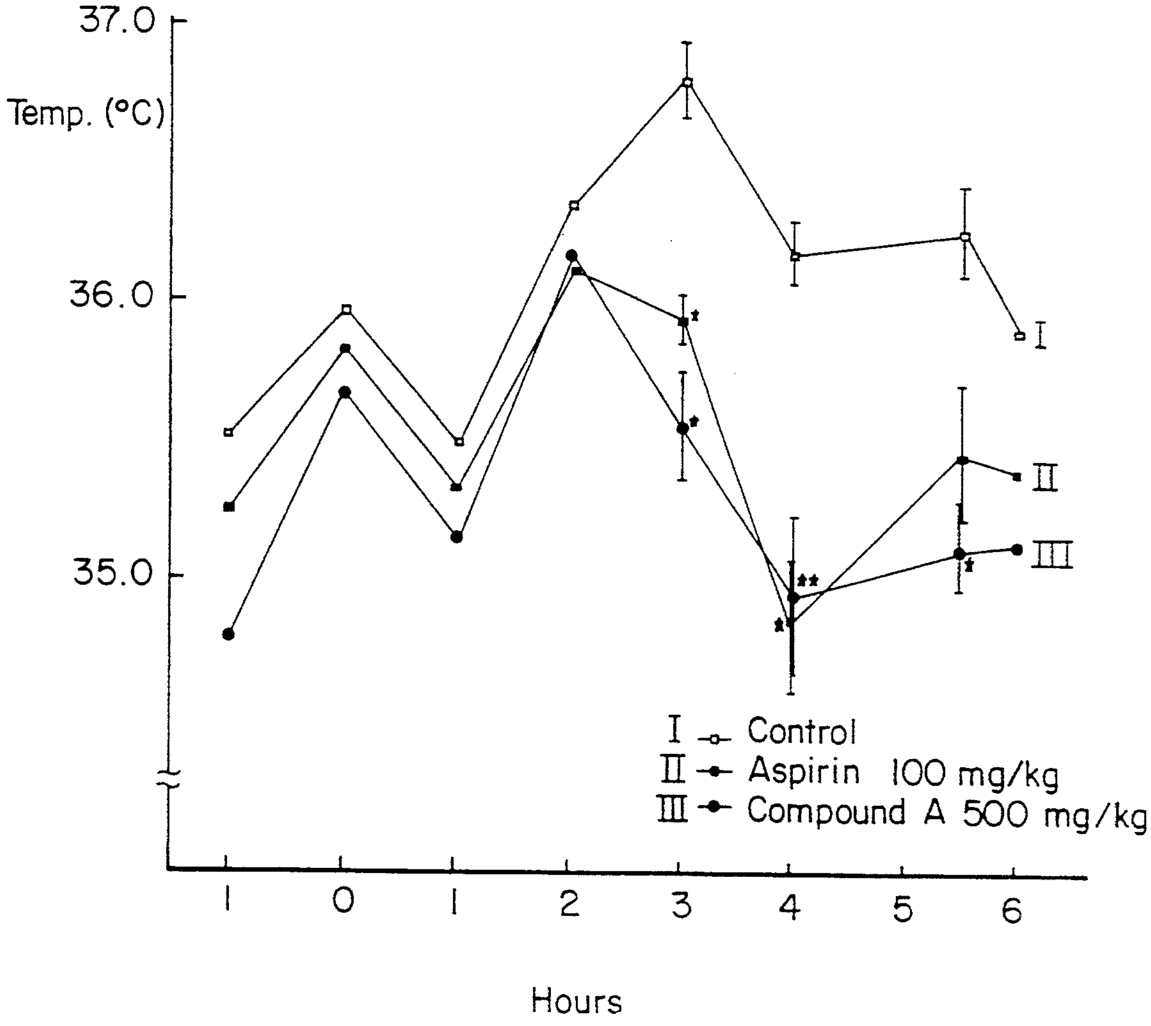
FIG. 3 illustrates the antipyretic effect of the compound described in Example 1.

Antipyretic activities were measured according to Winter et al. with some modifications (Winter, C. A. et al. (1963), *J. Pharmacol Exptl. Therap.*, 141, 309). Rectal temperature was measured using digitalized thermometer inserted 3 cm deep at one hr intervals. Typhoid vaccine was injected to mouse i.p. at zero time. After 2 hrs, aspirin and sample (compound in Example 1) were orally given to mouse. As shown in FIG. 3, the antipyretic potency of compound A was five times lower than that of aspirin.

TEST 3

A. Determination of Antiinflammatory Activity by Carrageenin-Induced Edema Test Animal: Male Sprague Dawley rats weighing approx. 170 g (5 rats as a group).
Sample: Compound A (300 mg/kg, 450 mg/kg in 1% CMC).
Reference: Phenylbutazone (100 mg/kg in 1% CMC)
Medication: Oral administration.

Experimental Procedures

The inhibitions of Carrageenin-induced edema by compound A and aspirin was measured according to Winster et al. (Winter, C. A., Risley, E. A. and Nuss, G. W. (1963), *J: Pharmaco. Exptl. Therap.*, 141, 369). Samples were administered orally at 6 hrs and 30 min before Carrageenin injection. Edema was induced with subcutaneous injection of 0.05 ml of 1% Carrageenin in saline solution in a hind paw of rat. Then, the volume of edema was measured at time intervals. The results are shown in Table II. It was determined that compound A had no anti-inflammatory effect when used at doses of 300 and 450 mg/kg.

TABLE II

Antiinflammatory Activity of Compound A

| Compound | Dose mg/kg P.O. | No. of Animals | % Increment of Edema (mean ± S.E.) 0.5 hr | 1.5 hr | 2.5 hr | 3.5 hr | 4.5 hr |
|---|---|---|---|---|---|---|---|
| Control | CMC | 5 | 28.1 ± 4.68 | 48.0 ± 7.51 | 55.9 ± 7.73 | 74.6 ± 24.06 | 73.4 ± 28.53 |
| Phenyl-butazone | 100 | 4 | 11.8 ± 6.26 | 20.9 ± 6.88 | 21.9 ± 9.22 | 36.2 ± 14.45 | 42.5 ± 6.35 |
| Compound A | 300 | 5 | 46.5 ± 13.98 | 51.2 ± 9.47 | 56.1 ± 11.50 | 69.4 ± 13.89 | 81.9 ± 9.96 |
| Compound A | 400 | 4 | 20.3 ± 6.85 | 33.8 ± 3.19 | 50.2 ± 6.43 | 58.4 ± 6.09 | 66.2 ± 8.52 |

B. Determination of Protein Stabilizing Activity

Sample: Compound A ($1 \times 10^{-3}$M in 5% DMF solution

Experimental Procedures

The protein stabilizng activity of the sample was analyzed as described by Mizushima (Mizushima, Y. (1965), *Lancet*, 1, 169). Briefly, 2 ml of 0.75% BSA in 0.1M phosphate-buffered saline (pH 5.3) was mixed with 1 ml of appropriately diluted test sample solution.

After standing at room temperature for 15 min, the reaction mixture was incubated at 66.5° C. and 0° C. for 3 min and 15 min, respectively. The degree of heat denaturation of BSA was estimated by the turbidity of colloidal precipitate, whose absorbance at 570 nm was measured. The results indicated that compound A did not contain protein stabilizing activity (data not shown).

C. Determination of Antithrombotic Activity

Animal: Male Sprague Dawley rate weighing 180–250 g.

Sample: Compound A ($1\times10^{-3}$M) in 5% DMF solution.

Experimental Procedures

Rats were anaesthetized with ether and 9 volumes of blood were collected by heart puncture with 1 volume of 3.12% sodium citrate. Combined blood samples were centrifuged at 1,200 rpm for 20 min at 4° C. to obtain platelet-rich plasma. Following centrifugation at 3,000 rpm for 10 min at 4° C., the resulting precipitates (platelets) were resuspended in 0.01M phosphate-buffered saline (pH 7.4). To 1 ml of this solution was added 0.1 ml of the sample solution. After 30 min incubation at 37° C., 10 units of thrombin was added and the reaction mixture was incubated for 1 hr. The platelet aggregation was not observed with naked eyes. Compound A ($1\times10^{-3}$M) showed antithrombotic activity.

TEST 4

Gastric Ulceration Experiment

Animal: Male Sprague Dawley rats weighing 160–210 g (6 rats as a group).

Sample: Compound A (100 mg/kg, 200 mg/kg, 800 mg/kg in 1% CMC).

Reference: Aspirin (200 mg/kg in 1% CMC).

Medication: Oral administration.

Experimental Procedures

The experiments of gastric ulceration were carried out according to Murakami et. al. (Murakami, M. et. al. (1982), *Jap. J. Pharmacol.,* 32, 299). Rats were deprived of food but allowed free access to water for 24 hrs (water was removed 2 hrs before experiments). Samples suspended in 1% CMC solution were removed. The stomachs were then inflated by injecting 10 ml of 2% formalin through the esophageal orifice and immersed in 2% formalin for 10 min. Subsequently, the stomachs were incised along the greater curvature and the length of each leison in the glandular portion was measured. The sum of the lengths (mm) of all lesions for each rat was used as the ulcer index. The results are shown in Table III.

TABLE III

The effects of Aspirin and Compound A on the Gastric Ulceration in Rats

| Compound | Dose (mg/kg) P.O. | No. of Animals | Ulcer Index (mm) (mean ± S.E.) |
|---|---|---|---|
| Control | 0 | 6 | 0 |
| Aspirin | 200 | 5 | 29.3 ± 6.15(5/5) |
| Compound A | 100 | 5 | 0 |
| Compound A | 200 | 6 | 0 |
| compound A | 800 | 6 | 0.7 ± 0.61(1/6) |

The number in parenthesis indicates the number of rats that exhibited gastric ulcer.

The results indicated that compound A did not cause gastric ulcer at 5 times higher dose than aspirin.

TEST 5

Determination of the Bleeding Time

To the experimental groups, equivalent doses of compound A and aspirin were administered separately for 10 days.

As shown Table IV, compound A prolonged the bleeding time by 50%.

TABLE IV

The Effects of Aspirin and Compound A on the Bleeding Time

| Compound | Dose (mg/kg) P.O. | No. of Animals | Bleeding Time Days 2 | 4 | 6 | 8 | 10 |
|---|---|---|---|---|---|---|---|
| Control | 0 | 7–9 | 238.3 ± 45.6 | 388.2 ± 33.8 | 391.1 ± 38.9 | 339.1 ± 54.5 | 314.8 ± 42.3 |
| Aspirin | 15 | 7–9 | 353.5 ± 74.7 | 372.7 ± 50.1 | 516.6 ± 119.4 | 493.6 ± 86.6 | 441.9 ± 46.2 |
| Compound A | 15 | 6–9 | 339.6 ± 53.9 | 396.9 ± 56.0 | 429.4 ± 50.6 | 518.3 ± 102.8 | 472.1 ± 57.4 (50)* |
| | 45 | 8 | | | | | 467.8 ± 55.9 (48)* |

The number in parenthesis indicates percent increment.
*Significance, $P < 0.05$

TEST 6

Acute Toxicity Test

When administered orally, compound A showed little toxicity in mouse ($LD_{50}=2.14$ g/kg).

In conclusion, the compound described in the present invention exhibited an antioxidant activity at concentrations higher than $2.5\times10^{-4}$M and an equivalent antipyretic activity at five times higher dose compared to aspirin.

On the other hand, compound A showed little side effects as it did not cause gastric ulceration, whereas aspirin at four times lower dose caused ulceration.

Therefore, the compound described in the present invention is a new acetylsalicylate derivative which sustains the antioxidant activity of the maltol derivatives and exhibits the antipyretic and antiinflammatory activities.

What is claimed is:

1. A compound of the following formula I

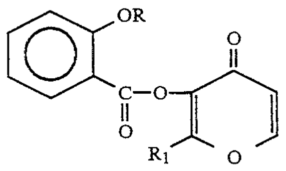

(I)

wherein R represents H, alkyl group containing $C_{1-5}$ carbon atoms or alkanoyl group containing $C_{1-5}$ carbon atoms, $R_1$ represents H or alkyl group containing $C_{1-5}$ carbon atoms.

* * * * *